United States Patent [19]

Tornier

[11] Patent Number: 4,677,972
[45] Date of Patent: Jul. 7, 1987

[54] COUPLING ASSEMBLY FOR JOINING AN IMPLANT TOOL TO A BONE IMPLANT

[76] Inventor: Alain Tornier, Le Brocey, 38130 Crolles, France

[21] Appl. No.: 826,450

[22] Filed: Feb. 5, 1986

[30] Foreign Application Priority Data

Feb. 7, 1985 [FR] France ................................. 85 01915

[51] Int. Cl.⁴ ................................................. A61F 5/04
[52] U.S. Cl. ............................... 128/92 V; 128/92 VP; 623/22
[58] Field of Search ............... 128/92 XT, 92, 92 XY, 128/92 XP, 92 VT, 92 V, 92 VY, 92 VP; 623/22

[56] References Cited

U.S. PATENT DOCUMENTS

| | | | |
|---|---|---|---|
| 2,528,941 | 11/1950 | Bassett et al. ................... | 128/92 XT |
| 3,685,058 | 8/1972 | Tronzo .............................. | 128/92 XT |
| 3,801,989 | 4/1974 | McKee .............................. | 128/92 XT |
| 4,399,813 | 8/1983 | Barber .............................. | 128/92 XT |
| 4,426,861 | 10/1984 | Dimakos et al. ................ | 128/92 XT |
| 4,531,517 | 7/1985 | Ferte et al. ...................... | 128/92 XT |

Primary Examiner—C. Fred Rosenbaum
Assistant Examiner—C. W. Shedd
Attorney, Agent, or Firm—Dowell & Dowell

[57] ABSTRACT

A quick disconnect coupling assembly for securing a bone implant to the tool for positioning the implant wherein the coupling assembly is carried by the tool and includes axially extending undercut teeth which are receivable within undercut notches formed in the peripheral face of the implant and which are locked therein by an axially reciprocating slideable shim assembly to thereby selectively unite the positioning tool to the implant.

3 Claims, 5 Drawing Figures

COUPLING ASSEMBLY FOR JOINING AN IMPLANT TOOL TO A BONE IMPLANT

BACKGROUND OF THE INVENTION

1. Field of the Invention

The present invention relates to a device for assembling a bone implant and the tool for positioning it and particularly to a coupling device which permits the tool and implant to be quickly assembled by axially adjustable shims which selectively lock axially oriented teeth carried by the tool with undercut notches formed in the face of the implant.

2. History of the Art

Bone implants such as artificial acetabula for the femur head, made of metal or plastic material, are known to be provided on their periphery with one or more threads of cylindrical, truncated or spherical form which are used to secure the implant in the bone.

Three systems for positioning such bone implants exist at the present time:

A first method requires that a prior tapping be made in the hip bone so that when the acetabulum is to be replaced, the prosthesis is screwed in position within the tapped opening;

In certain cases, the outer thread of the prosthesis is in the form of a tap so as to allow the prosthesis to be positioned or implanted directly in the bone.

In those instances where the prosthesis comprises a metallic element provided with a cup made of plastic material, the cup is placed in position after the metallic element is implanted in the bone.

The object of the improvements forming the subject matter of the present invention is to facilitate positioning or implanting of artificial acetabula.

Most systems for positioning known at present comprise an implantation element or handle which is freely movable with respect to the acetabulum, this making it impossible to accurately control the direction or orientation of the artificial acetabulum during the implantation operation.

In French Patent No. 77 20235 a system for fixing the artificial acetabulum is disclosed, in which assembly screws are used to join the implantation tool to the acetabulum employing a wrench. However, taking into account the operational conditions, this system is difficult to use and the parts are difficult to separate as such separation must be effected directly in the location of the joint or connection. Moreover, dismantling of the assembly by removal of the screws is a long operation, leading to a loss of time which is detrimental for the patient and for the overall efficiency of the operation.

SUMMARY OF THE INVENTION

According to the invention, the artificial acetabulum is modified to include a peripheral annular flange in which notches are made. The notches include at least one undercut wall. The implantation element is in the form of a handle provided with wedge-shaped teeth extending from the forward end thereof which may be engaged in the notches so that the oblique face of the wedges comes into abutment against the undercut wall of the notches. A shim assembly is thereafter moved axially so that the shims carried are engaged in the notches and thereby bind the teeth of the handle therein. The handle may include a handhold constituted by an oblique bar which is associated with a known tool, for example of the ratched handle type. In this way, the handle makes it possible to maintain the desired orientation of the geometrical axis of the acetabulum perfectly, while the bar of the known tool is used for rotating the prosthesis which is placed in position by direct tapping thus avoiding the need for prior tapping and therefore the difficulty of finding and aligning the thread already machined in the acetabulum when positioning the prosthesis. If the prosthesis is composite, i.e. if it comprises an outer metallic element and an inner cup made of plastic material, such as composite prosthesis may be positioned directly when the two elements have been preassembled in the factory and not during the operation. This will further reduce the length of the operation.

BRIEF DESCRIPTION OF THE DRAWINGS

The invention will be more readily understood on reading the following description with reference to the accompanying drawings, in which.

DESCRIPTION OF THE PREFERRED EMBODIMENT

Figure 1:
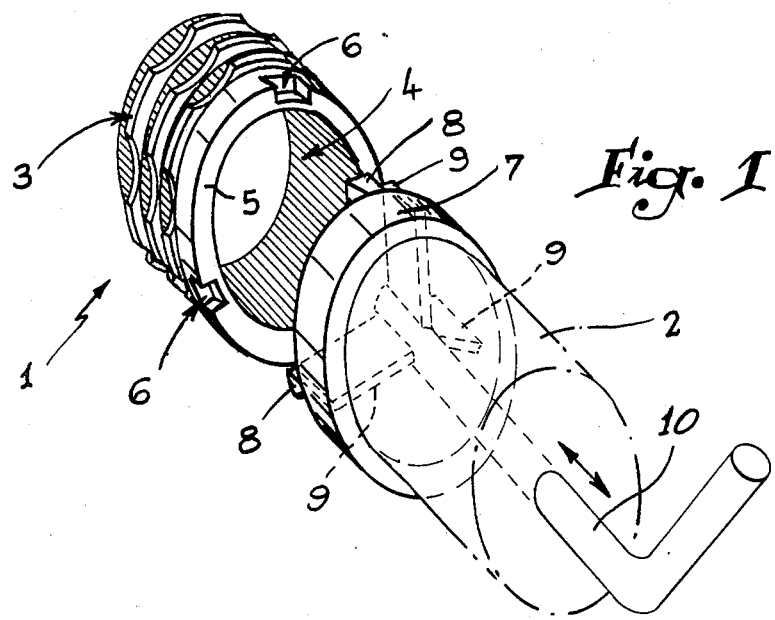
FIG. 1 is a view in perspective of an assembly or coupling device according to the invention.

Referring now to the drawings, the assembly device according to the invention is intended for connecting an implant 1, for example an artificial acetabulum, and a positioning or implanting tool or handle 2 illustrated in broken lines in FIG. 1.

The periphery 3 of the acetabulum 1 takes the form of a conventional threaded tap which has simply be shown by broken lines in order not to complicate the drawing. Of course, this tap may have one or more threads. Around its central cavity 4, the acetabulum includes an annular flange 5 provided with three notches 6. As illustrated, each notch is in the form of a right-angled trapezoid of which the shortest side corresponds to the opening 6a of the notch and the longest side 6b to the bottom thereof. These two sides are joined by a wall 6c extending normally thereto and by an oblique undercut wall 6d.

Figure 2:
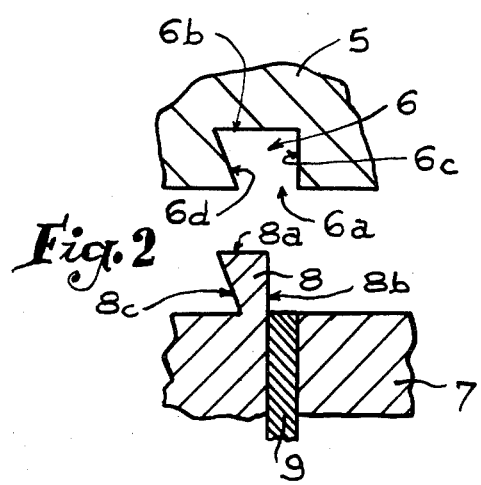
FIGS. 2 to 5 show the manner in which the two parts of the coupling device are locked one with respect to the other.

The handle or tool includes a ring 7 at one of its ends having axial wedge-shaped teeth 8 in a number identical to the number of notches 6 and oriented in the same manner. Ring 7 has the same outer diameter as flange 5 so that the teeth 8 can engage freely in notches 6. To this end, and as illustrated in FIG. 2, each tooth 8 is in the form of a right-angled trapezoid of which the sides are shorter than those of notches 6. In particular, the long side 8a of the tooth is smaller than the shortest side 6a or opening of notch 6 so that the tooth can be freely engaged therein. The height of each tooth 8 is sligntly greater than the depth of the notches.

Side 8b of each tooth which is oriented perpendicularly to its face 8a. An axially movable shim 9 is selectively slideable between sides 8b of each tooth and the sides 6c of each notch. The thickness of the shim are such that, when each shim is placed next to a tooth 8, these two members form an assembly whose shape corresponds exactly to that of notch 6 thereby locking the teeth within the notch.

Shims 9 are made to slide by means of a conrol rod 10 accessible at the end of the tool or handle opposite ring 7.

Figure 3:
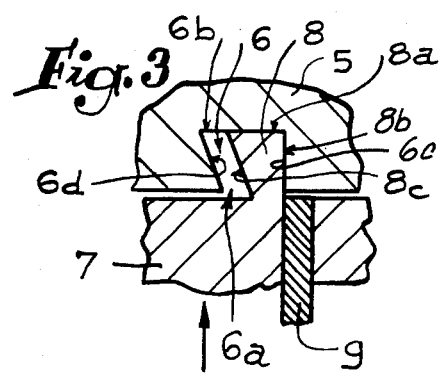
Figure 4:
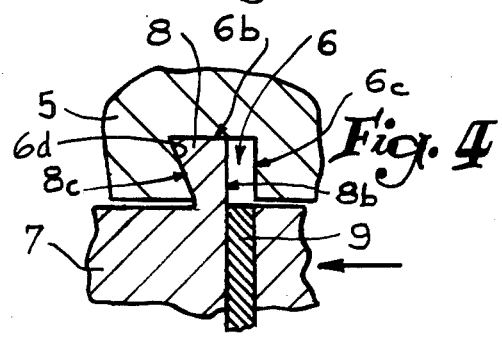
Figure 5:
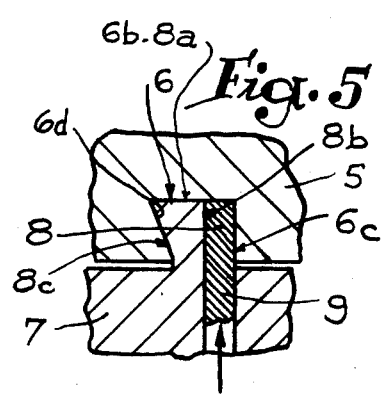

Handle or tool 2 and implant 1 are connected as illustrated in FIGS. 3 to 5. The three teeth 8 are firstly engaged in the corresponding three notches 6 by an axial movement of the handle with respect to the implant, then, the implant being fixed, the handle is rotated slightly so that the oblique sides 8c of teeth 8, whose slope is the same as that of walls 6d of the notches, come into abutment against the latter (FIG. 4). Finally, the last operation consists in displacing the three shims 9 simultaneously in the axial direction by control rod 10 so that they penetrate in the notches 6 and maintain the teeth compressed with respect to the notches so that the oblique face 8c of each tooth is blocked against the oblique wall 6d of the corresponding notch. After this operation, handle 2 and prosthesis 1 are firmly joined and united.

As indicated hereinabove, the handle or tool 2 may include a ratchethandle so that a ring having a pawl may drive this handle in rotation in one direction or the other, for example by means of an oblique rod secured with the ring.

It must, moveover, be understood that the foregoing description has been given only by way of example and that it in no way limits the domain of the invention which would not be overcome by replacing the details described by any other equivalents.

What is claimed is:

1. A coupling assembly for securing a bone implant such as an artificial acetabulum to a tool for use in implanting the implant comprising the bone implant having an annular flange mounted thereto, said annular flange having a front face, a plurality of notches formed in spaced relationship with respect to one another in said front face of said annular flange, each of said notches having at least one undercut wall portion, the tool having a forward annular end portion having a plurality of wedge shaped teeth extending outwardly therefrom in generally parallel relationship to the axis of the tool, each of said wedge shaped teeth of the tool being of a size to be cooperatively received within said notches in said annular flange so as to create a space adjacent thereto in each notch, a plurality of shim means slideably carried by the tool adjacent each of said wedge shaped teeth so as to be axially movable with respect thereto, and means for simultaneously moving said shim means so as to enter said spaces within said notches to thereby bind each of said wedge shaped teeth within said notches and thereby lock the tool to the bone implant.

2. The coupling assembly of claim 1 in which each of said wedge shaped teeth are integrally mounted to a ring carried by the tool and extending forwardly thereof, said ring being complementary in size to the annular flange mounted to the bone implant.

3. The coupling assembly of claim 2 in which each of said notches is in the configuration of a trapezoid and wherein each of said wedge shaped teeth are also in the configuration of a trapezoid wherein the tapered walls of each trapezoidal configuration are in abutting contact with one another when said wedged shaped teeth are engaged within said notches.

* * * * *